(12) United States Patent
Epitropoulos

(10) Patent No.: US 6,783,239 B2
(45) Date of Patent: Aug. 31, 2004

(54) GLARE TESTER ATTACHMENT

(76) Inventor: Alice T. Epitropoulos, 340 E. Town St., Suite 8-200, Columbus, OH (US) 43215-4619

(*) Notice: Subject to any disclaimer, the term of this patent is extended or adjusted under 35 U.S.C. 154(b) by 44 days.

(21) Appl. No.: 10/099,119

(22) Filed: Mar. 18, 2002

(65) Prior Publication Data
US 2003/0174283 A1 Sep. 18, 2003

(51) Int. Cl.$^7$ .................................................. A61B 3/10
(52) U.S. Cl. ...................................................... 351/221
(58) Field of Search ................................ 351/201, 203, 351/21, 213, 221, 237, 239, 243, 211

(56) References Cited

U.S. PATENT DOCUMENTS 4,800,404 A * 1/1989 Ginsburg et al. ........... 351/243
6,099,126 A * 8/2000 Teskey ....................... 351/213

* cited by examiner

Primary Examiner—George Manuel
(74) Attorney, Agent, or Firm—Porter, Wright, Morris & Arthur, LLP

(57) ABSTRACT

An ophthalmic glare tester for evaluating visual acuity under conditions of strong diffuse illumination is designed for convenient mounting on a conventional ophthalmic instrument such as a transilluminator or ophthalmoscope. The glare tester incorporates a generally concave reflector for providing diffuse illumination to an eye and a mounting for attachment to an ophthalmic instrument. The reflector includes a wall having an interior light-reflecting surface at least partially enclosing a hollow interior. The glare tester provides for conducting illumination from the ophthalmic instrument to the interior light reflecting surface of the reflector.

20 Claims, 9 Drawing Sheets

GLARE TESTER ATTACHMENT

BACKGROUND OF THE INVENTION

1. Field of the Invention

This invention relates to a glare tester and more specifically to a glare tester attachment suitable for use with a standard ophthalmic instrument.

2. Brief Description of the Prior Art

In recent years it has been discovered that the visual acuity of a patient measured in a standard dark refracting lane in an ophthalmologist's or optometrist's office may not be indicative of the patient's acuity in conditions of bright light or glare, especially where the patient suffers from eye disorders such as cataracts or corneal scars. In order to provide a more thorough assessment of a patient's visual acuity, brightness acuity or "glare" testers have been devised. One type of glare tester subjects the eye to be tested to a bright generally uniform illumination while the patient observes a test chart, e.g., a standard Snellen chart. This "brightness acuity test" provides an objective measurement of visual acuity under bright light conditions. It is useful to evaluate visual problems caused by cataracts, corneal scarring, and other conditions that cause intraocular light scattering. Alternatively, the eye may be subjected to a macular photostress test to detect possible maculopathy. In the photostress test, the visual acuity of the eye is first determined under conventional testing conditions. The eye is then subjected to bright illumination for a certain length of time ("photostress conditions"). The eye's acuity is retested under conventional conditions after one or more resting intervals to permit recovery of the retina. The period required for recovery of normal visual acuity is indicative of possible macular disturbances, e.g., cystoid macular edema or senile macular degeneration. A glare tester suitable for performing such tests is disclosed in, for example, U.S. Pat. No. 4,784,483 to Holladay et al., the entire disclosure of which is incorporated herein by reference.

Such a glare tester comprises an illumination source of predetermined intensity situated in an open-sided, generally concave illumination chamber sized to occlude the tested eye. The interior of the chamber is provided with a diffusively reflective wall, whereby the eye is subjected to a generally uniform illumination. A test chart may be viewed through an aperture in the chamber wall opposite the eye to perform a brightness acuity test. Alternatively, the viewing aperture may be occluded to provide a photostress to the eye for a predetermined period, after which the visual acuity is tested to evaluate the effect of the photostress on vision as described above.

A glare tester of this type typically comprises a handle containing a source of power, e.g., batteries, with the illumination chamber mounted at one end of the handle. In use, the illumination chamber is held in position in front of the eye to be tested by the patient or examining ophthalmologist. The patient then follows the instructions of the examiner in performing a brightness acuity test or a photostress test as described above.

Although such glare testers have made this form of acuity testing relatively convenient and have encouraged such testing, the currently available glare testers of this type have certain disadvantages. Current testers are marketed as separate instruments that require the use of a separate charging unit and are not capable of being recharged in a standard recharging well used for other examination instruments such as ophthalmoscopes, retinoscopes, and transilluminators.

Furthermore, even if a separate glare tester were compatible with standard recharging units, such units typically do not provide enough charging wells to accommodate a glare tester in addition to the conventional ophthalmic examination instruments. Consequently, an entire separate instrument and recharger must be purchased in order to conduct glare testing.

Accordingly, a need has continued to exist for a simple and inexpensive glare testing apparatus, preferably usable with standard ophthalmic examination instruments.

SUMMARY OF THE INVENTION

The need has been alleviated by the present invention, which, according to its various aspects, provides a glare testing attachment that can be mounted on a conventional transilluminator or ophthalmoscope so as to use the light source provided in those instruments.

Accordingly, the glare tester of the invention incorporates

- a generally concave reflector for providing diffuse illumination to an eye, the reflector comprising a wall having an interior light-reflecting surface partially enclosing a hollow interior chamber;
- mounting means for removably supporting the reflector on a source of illumination; and
- means for conducting illumination from the source of illumination to the interior light reflecting surface.

Accordingly, it is an object of the invention to provide an instrument for testing the effect of glare on visual acuity.

A further object is to provide a convenient and inexpensive glare tester.

A further object is to provide a glare tester that can be attached to a standard transilluminator.

A further object is to provide a glare tester that can be attached to a standard ophthalmoscope.

A further object is to provide a glare tester that can be recharged in a standard ophthalmic recharging well.

Further objects of the invention will be apparent from the description of the invention which follows.

DETAILED DESCRIPTION OF THE INVENTION AND PREFERRED EMBODIMENTS

Figure 1:
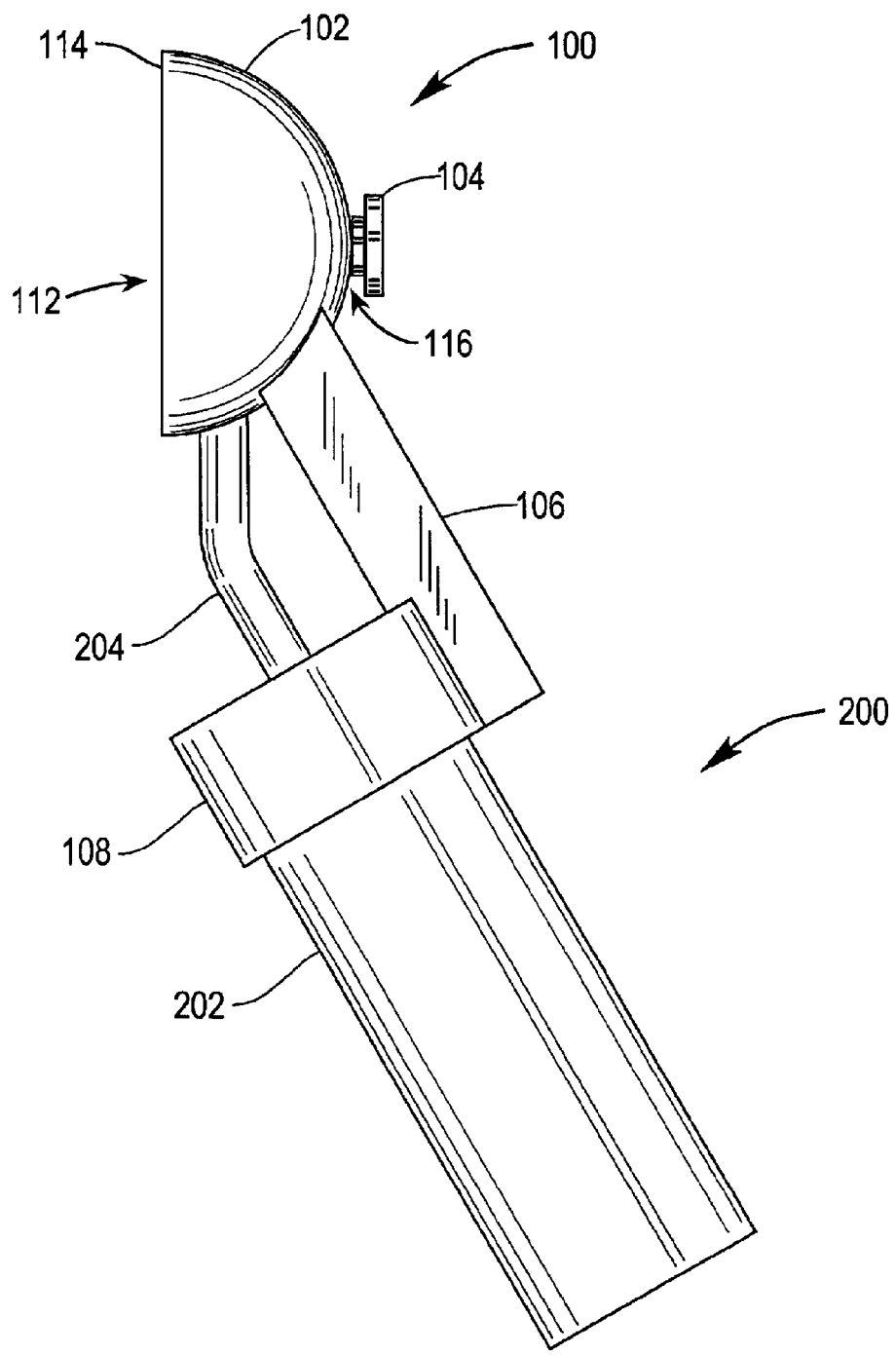
FIG. 1 illustrates a side elevational view of one embodiment of the glare tester of the invention mounted on a standard transilluminator.

According to the invention a glare tester incorporates a generally concave reflector for providing diffuse illumination to an eye, the reflector comprising a wall having an interior light-reflecting surface at least partially enclosing a hollow interior chamber, mounting means for removably supporting the reflector on a source of illumination; and means for conducting illumination from the source of illumination to the interior light reflecting surface.

The concave reflector of the invention comprises a chamber having a wall partially surrounding a hollow interior. One side of the chamber has an opening generally sized to cover the orbit when placed in front of the eye. Accordingly, the orbital opening of the reflector is bounded by a rim, which may have any convenient shape. Thus the orbital opening of the reflector may be circular, elliptical, rectangular, or the like. A preferred shape for the orbital opening of the reflector is circular.

The depth of the illumination chamber defined by the wall may be any convenient depth. Accordingly the cross-sectional shape of the wall may be semicircular, semielliptical, rectangular, or the like. Suitable cross sections for the illumination chamber are disclosed in U.S. Pat. No. 4,784,483. A preferred cross-sectional shape is semicircular. Thus a preferred shape for the reflector used in the glare tester of the invention is hemispherical. In another preferred embodiment the reflector may have a frustopyramidal shape.

The interior wall of the reflector should be light-reflective in order to distribute illumination introduced into the reflector generally uniformly over the visual field of the test eye. It is preferred that the interior of the wall have a white, perfectly diffuse reflective surface. However, any surface that provides an approximately uniform illumination, i.e., sufficiently uniform to simulate a typical glare environment, over the field of view of the test eye can be useful and is included within the concept of the invention.

The portion of the wall generally opposite the orbital opening may be defined as the apex of the reflector. In a preferred embodiment a visual aperture is formed in the apex of the reflector in order to permit the test eye to view a test chart while being subjected to the glare provided by the illuminated interior of the illumination chamber. The visual aperture may be provided with a plug, which can be introduced when a test chart is not observed during the illuminations as when photostress testing is performed on the eye.

According to the invention, the glare tester is illuminated using a standard ophthalmic instrument such as a transilluminator or ophthalmoscope. Accordingly, the reflector is provided with mounting means for attaching the reflector to a such a standard instrument, and positioning the reflector at the end of the handle of the instrument whereby light from the instrument can be directed into the glare tester. Any structure that so positions the reflector to receive light from the ophthalmic instrument is suitable. For example, a collar or clamp or the like can be mounted on the handle of the ophthalmic instrument and a bracket extending from the collar can hold the reflector in an appropriate position and orientation. Alternatively, a structure attached to the reflector can receive the transilluminator probe or ophthalmoscope head to support the reflector.

The reflector has an illumination aperture in the wall positioned to admit the light from the transilluminator or ophthalmoscope to the interior of the reflector. Furthermore, if necessary, one or more mirrors, prisms, or the like can be positioned in the supporting structure to direct the light form the ophthalmic instrument through the illumination aperture into the reflector.

The invention will now be illustrated by certain embodiments thereof, which are not intended to be limiting in any way, the scope of the invention being defined only by the appended claims.

Figure 2:
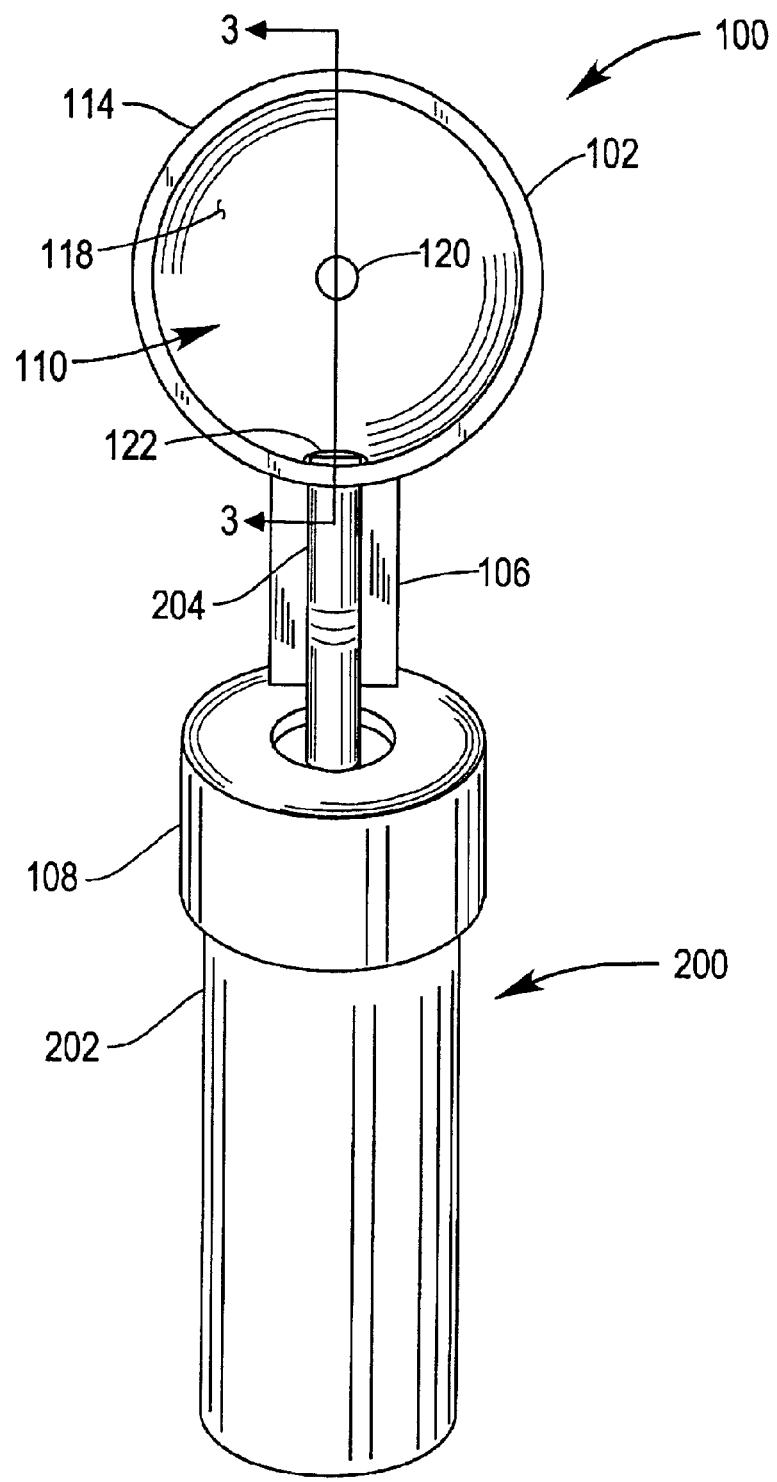
FIG. 2 illustrates a front elevational view of the glare tester of FIG. 1.
Figure 3:
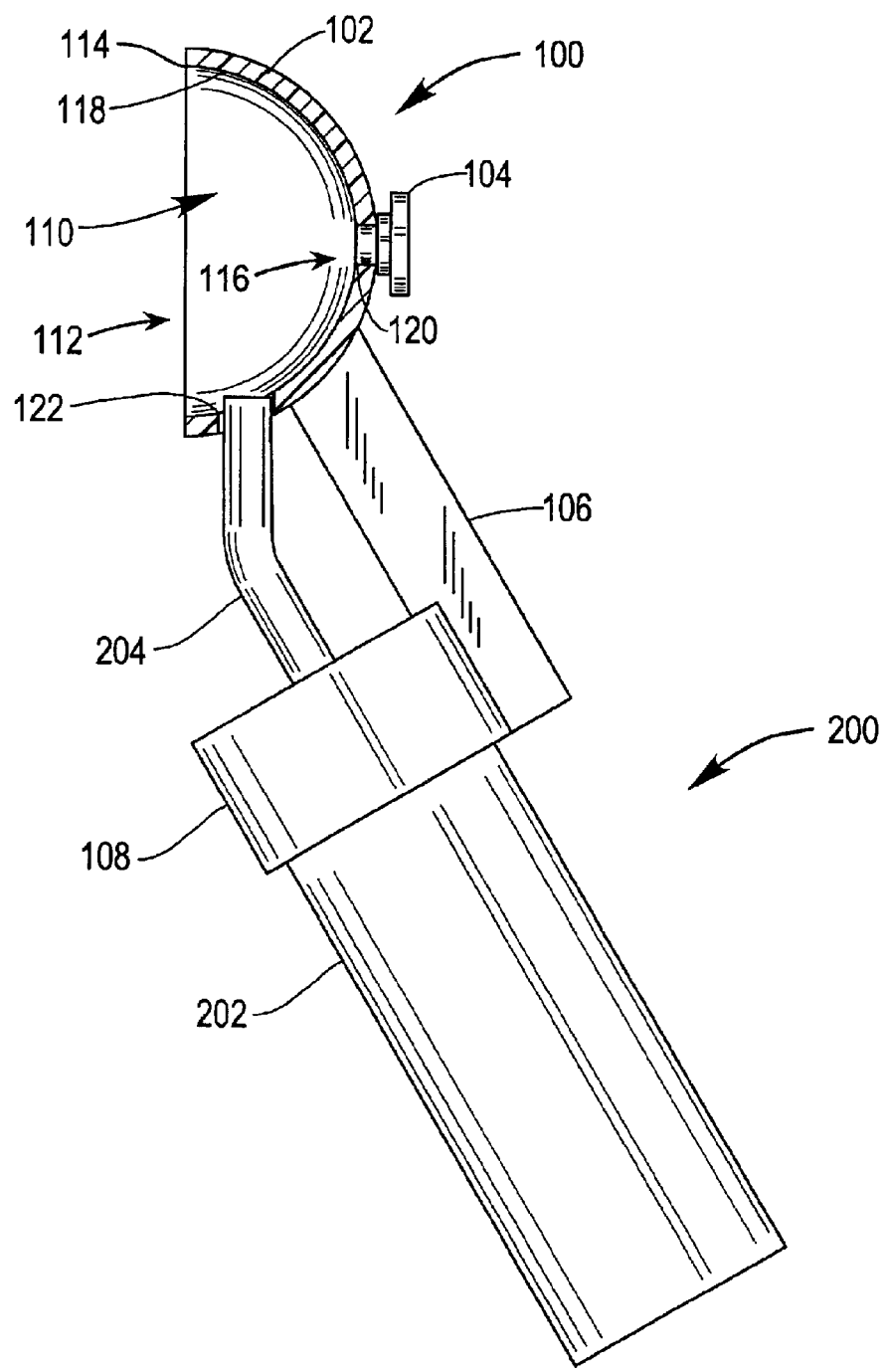
FIG. 3 illustrates a side elevation partial cross sectional view of the embodiment of FIGS. 1 and 2, taken along the line 3—3 in FIG. 2.
Figure 4:
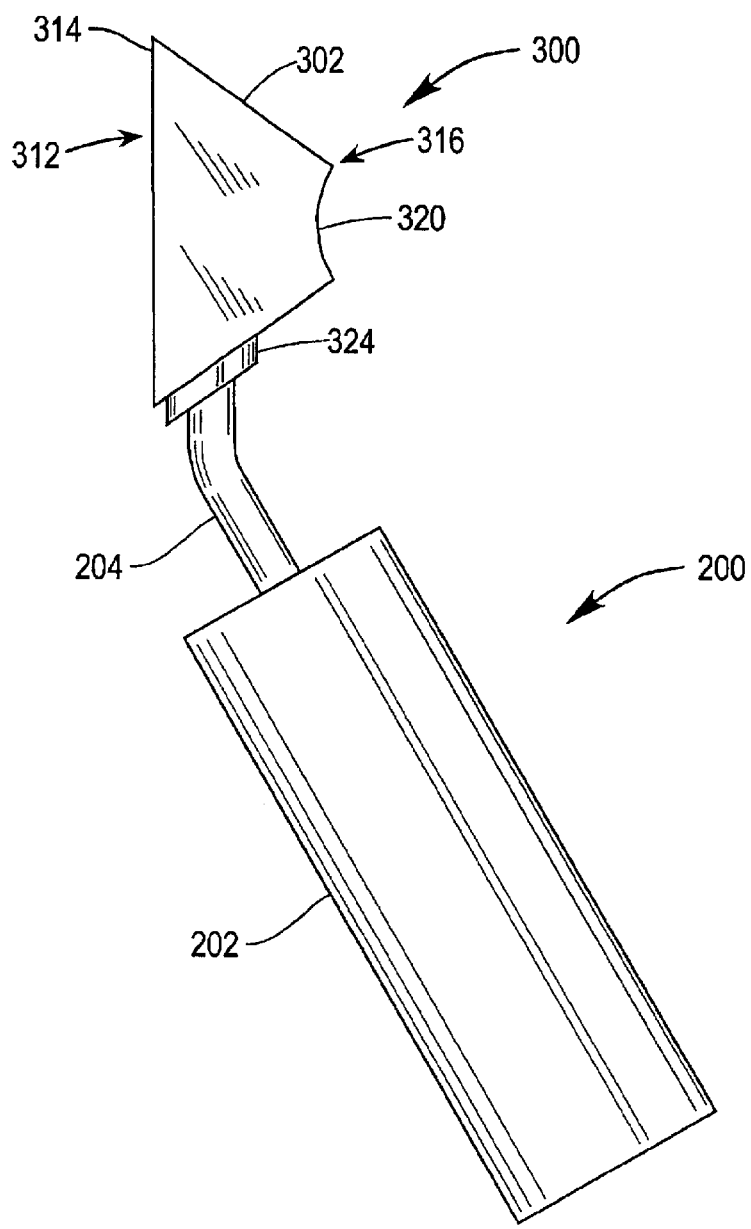
FIG. 4 illustrates a side elevational view of an embodiment of the invention designed for convenient mounting on a standard transilluminator.
Figure 5:
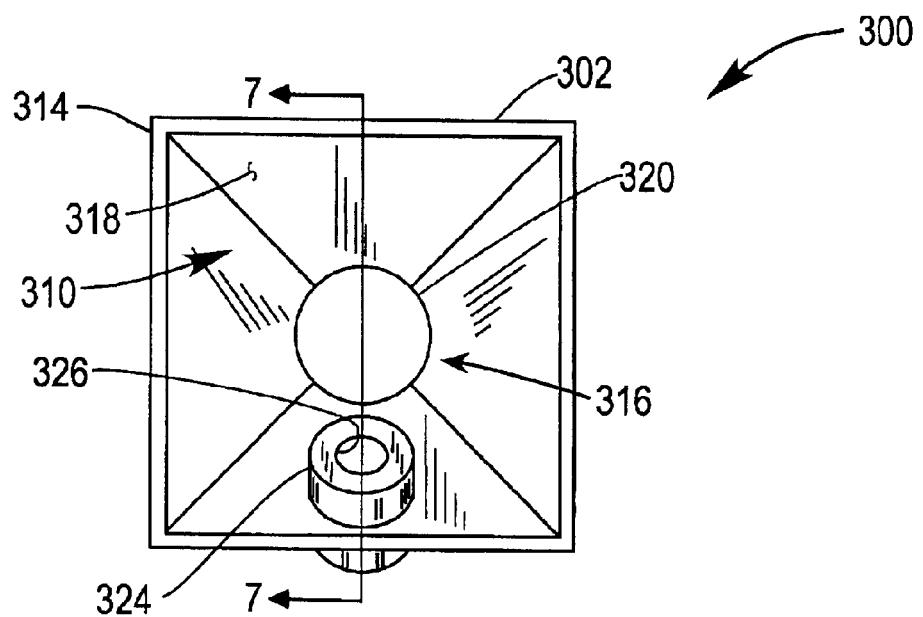
FIG. 5 illustrates a front elevational view of the glare tester of FIG. 4.
Figure 6:
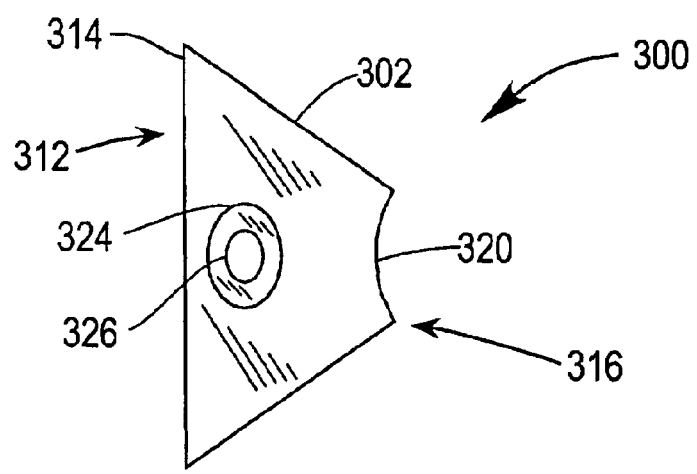
FIG. 6 illustrates a bottom view of the glare tester of FIG. 4.
Figure 7:
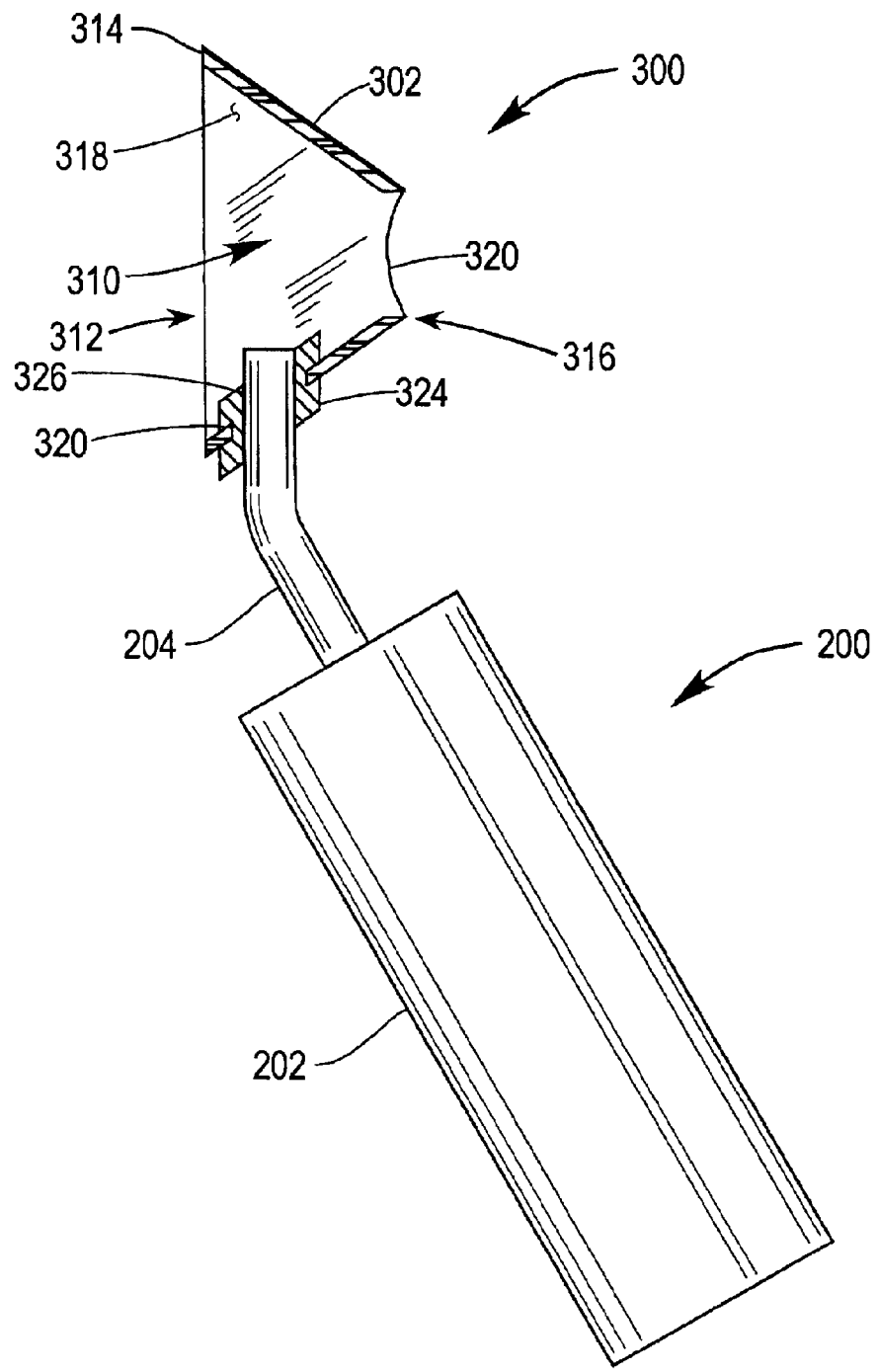
FIG. 7 illustrates a side elevational cross-sectional view of the glare tester of FIGS. 4–6 taken along the line 7—7 in FIG. 5.
Figure 8:
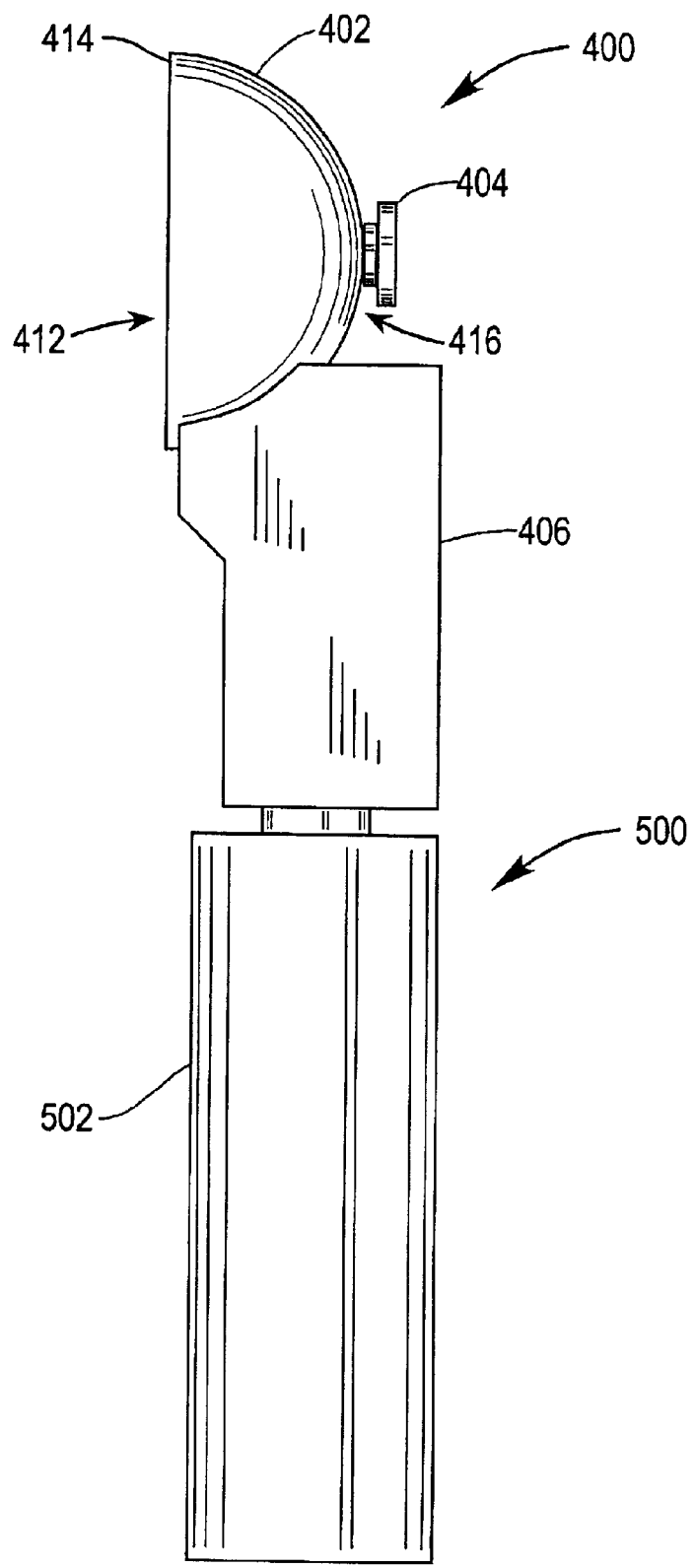
FIG. 8 illustrates an embodiment of the glare tester of the invention designed for mounting on a standard ophthalmoscope.
Figure 9:
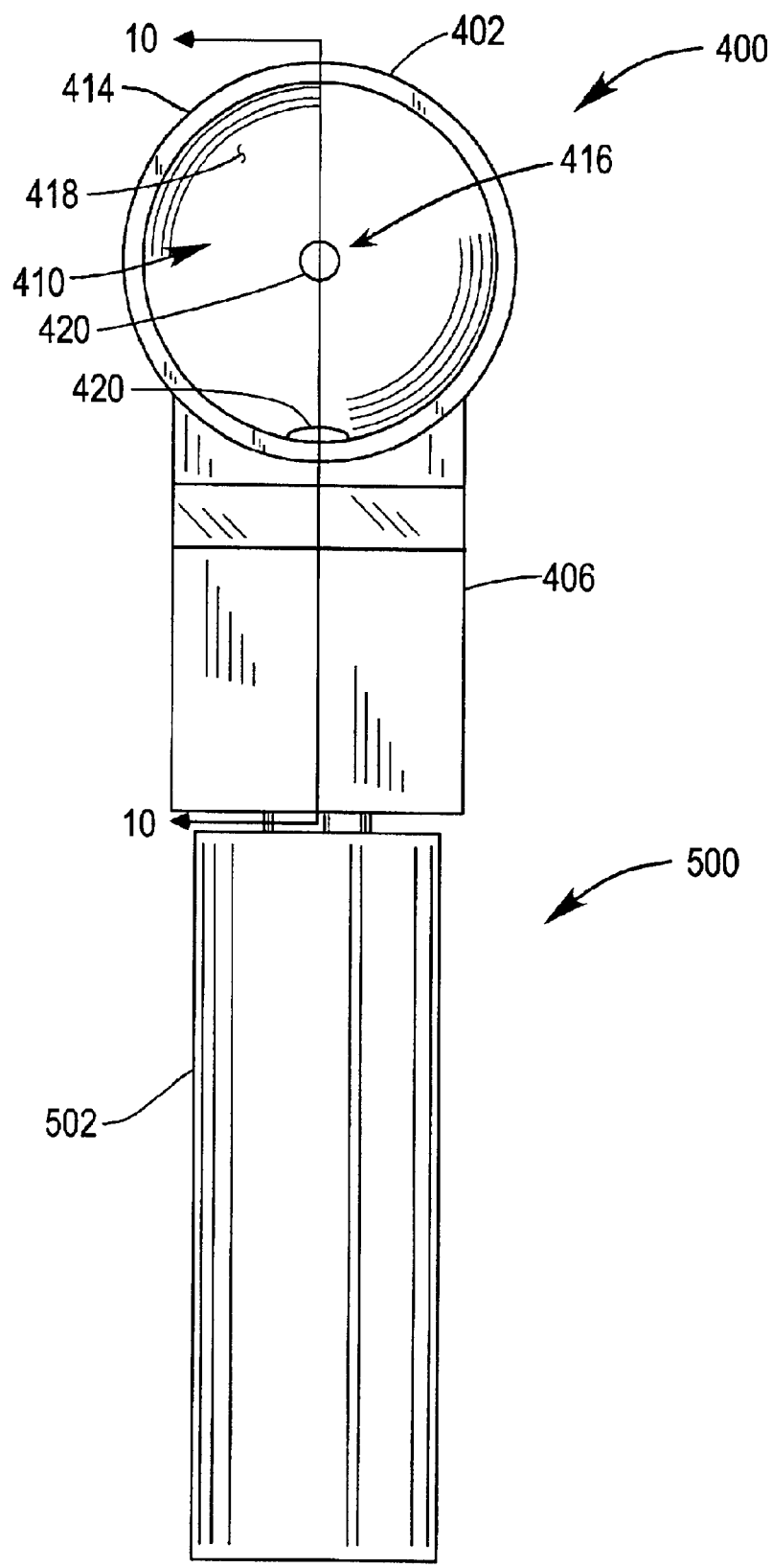
FIG. 9 illustrates a front elevational view of the glare tester of FIG. 8.
Figure 10:
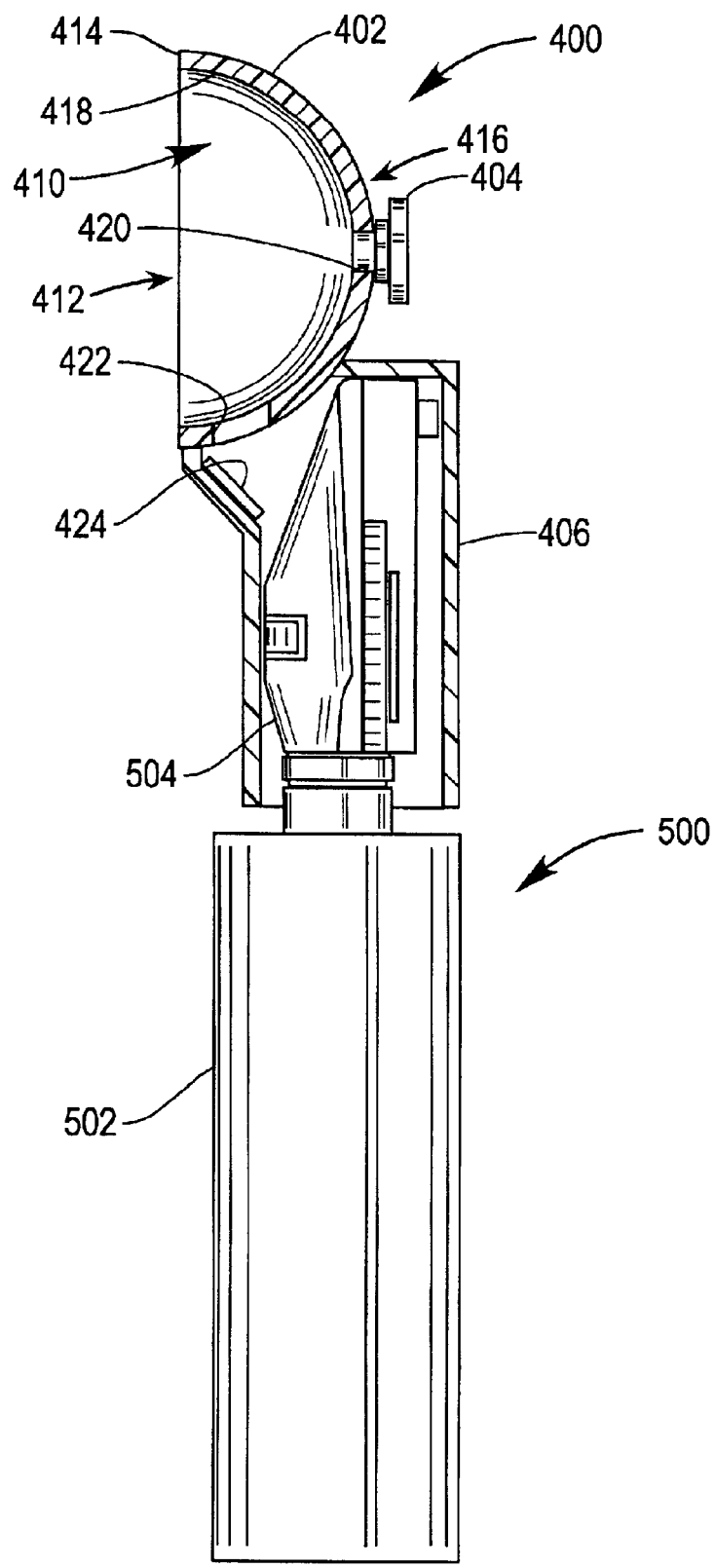
FIG. 10 illustrates a side elevation partial cross sectional view of the embodiment of FIGS. 8 and 9, taken along the line 10—10 in FIG. 9.

FIGS. 1–3 illustrate a glare tester 100 of the invention mounted on a conventional transilluminator 200 having a handle 202, containing a battery and a lamp, and a light-conducting probe 204. The glare tester 100 comprises a wall or shell 102 supported by a bracket 106 and a supporting collar 108 on the handle 202 of the transilluminator 200. The wall 102 surrounds an illumination chamber 110 having an open side 112, bounded by an orbital rim 114, and an apex 116. The interior surface 118 of the wall 102 is light reflective, and preferably as perfectly diffusive and light-reflective as possible. At the apex 116 of the wall 102 a viewing aperture 120 is formed to permit viewing of a test chart while an eye is being subjected to strong diffuse illumination. If a photostress test is to be performed, wherein the eye is first stressed by strong illumination and the visual acuity is tested after a recovery period, an occluding plug 104 may be inserted into the viewing aperture 120. An illumination aperture 122 in the bottom of the wall 102 receives the tip of the illumination probe 204 of the transilluminator 200. Accordingly, the transilluminator 200 serves as a source of light of the glare tester 100 whenever a glare test is to be performed. The glare tester 100 can be removed from the transilluminator 200 for conventional use of the instrument.

FIGS. 4–7 illustrate a preferred embodiment of the invention wherein a reflector 300 is mounted directly on the illumination probe 204 of a transilluminator 200. The reflector 300 has a wall 302 of a generally frustopyramidal shape. The wall 302 surrounds an illumination chamber 310 having an open side 312, bounded by an orbital rim 314, and an apex 316. The apex 316 of the wall 302 is provided with a viewing aperture 320. At the bottom of the wall 302 an illumination aperture 322 is formed. The illumination aperture 322 receives a grommet 324 having a central hole 326 sized to be a friction fit on the tip of the illumination probe 204 of the transilluminator 200. Preferably, the grommet 324 is made from a white elastomeric material, e.g., silicone rubber or white rubber, to provide good light-reflective properties together with a friction fit on the tip of the illumination probe 204. Thus the glare tester 300 may be conveniently and quickly mounted on the transilluminator 200 when a glare test is to be performed, and quickly removed for conventional use of the transilluminator.

FIGS. 7–10 illustrate an embodiment of the invention wherein a glare tester 400 according to the invention is mounted on a standard ophthalmoscope 500 having a handle 502 containing a battery, and a head 504.

The reflector 402 of the glare tester 400 is similar to the glare tester 100 shown in FIGS. 1–3. The glare tester 400 comprises a wall or shell 402 having an interior light-reflecting surface 410. The wall 402 surrounds an illumination chamber 410 having an open side 412, bounded by an orbital rim 414, and an apex 416. At the apex of the wall 402 a viewing aperture 420 is formed to permit viewing of a test chart while an eye is being subjected to strong diffuse illumination. If a photostress test is to be performed, an occluding plug 404 may be inserted into the viewing aperture 420. An illumination aperture 422 is formed in the bottom of the wall 402 to admit illumination from the ophthalmoscope 500.

The wall 402 of the glare tester 400 is mounted on a socket 406 that receives the head 504 of the ophthalmoscope 500. When the glare tester 400 is mounted on the ophthalmoscope 500, light therefrom is reflected by mirror 424 through the illumination aperture 422 into the interior of the reflector 402.

The wall of the glare tester can be made of any suitable material, e.g., metal, synthetic resin, or the like. If the wall is made of metal or a plastic that does not provide a white diffusively reflective interior surface, the interior surface is provided with a light-reflective surface, preferably highly diffusive, e.g., by a white paint or the like. Similarly, the supporting means can be made of any suitable material, e.g., metal, plastic, or the like. The design of the mounting means and adapter for attaching to a standard ophthalmic instrument will vary depending on the particular instrument with which the glare tester is to be used. Design of such support elements is conventional and within the skill of the ordinary practitioner.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than the foregoing description, and all changes which come within the meaning and range of equivalency of the claims are intended to be embraced therein.

I claim:

1. A glare tester attachment for use with a conventional hand-held ophthalmic instrument having a source of illumination, said glare tester attachment comprising:
    a generally concave reflector, said reflector comprising a wall partially enclosing a hollow interior chamber, said wall having an interior light-reflecting surface;
    mounting means for removably supporting said reflector on the conventional hand-held ophthalmic instrument; and
    means for directing said illumination to said interior light reflecting surface.

2. The glare tester attachment of claim 1, wherein said hollow interior chamber has an open side and a closed side, said closed side being bounded by said concave reflector and said reflector having an apex located opposite said open side.

3. The glare tester attachment of claim 1, wherein said reflector is generally hemispherical.

4. The glare tester attachment of claim 1, wherein said reflector is generally frustopyramidal.

5. The glare tester attachment of claim 2, wherein said reflector has a viewing aperture generally at said apex of said reflector.

6. The glare tester attachment of claim 1, wherein said mounting means comprises means for attaching said reflector to a probe of an ophthalmic transilluminator.

7. The glare tester attachment of claim 6, wherein said mounting means comprises a grommet in said reflector sized to accept said probe of said ophthalmic transilluminator.

8. The glare tester attachment of claim 1, wherein said means for directing illumination includes an illumination aperture in said reflector for admitting light from said source of illumination to said interior of said reflector.

9. The glare tester attachment of claim 8, wherein said mounting means includes means for positioning a tip of a probe of an ophthalmic transilluminator to direct light through said illumination aperture.

10. The glare tester attachment of claim 1, wherein said mounting means includes a socket for receiving an ophthalmoscope.

11. The glare tester attachment of claim 10, wherein said means for directing illumination includes a mirror for directing light from said ophthalmoscope into said interior of said reflector.

12. The glare tester attachment of claim 1, wherein the conventional hand-held ophthalmic instrument is an ophthalmic transilluminator.

13. The glare tester attachment of claim 1, wherein the conventional hand-held ophthalmic instrument is an ophthalmoscope.

14. A glare tester attachment for use with a conventional hand-held ophthalmic transilluminator having a probe and a source of illumination, said glare tester attachment comprising:
    a generally concave reflector, said reflector comprising a wall partially enclosing a hollow interior chamber, said wall having an interior light-reflecting surface;
    mounting means for removably supporting said reflector on the conventional hand-held ophthalmic transilluminator;
    means for directing said illumination to said interior light reflecting surface;
    wherein said hollow interior chamber has an open side and a closed side and said reflector has an apex located opposite said open side; and
    wherein said reflector has a viewing aperture generally at said apex of said reflector.

15. The glare tester attachment of claim 14, wherein said mounting means comprises means for attaching said reflector to the probe.

16. The glare tester attachment of claim 14, wherein said mounting means comprises a grommet in said reflector sized to accept the probe.

17. The glare tester attachment of claim 14, wherein said means for directing illumination includes an illumination aperture in said reflector for admitting light from the source of illumination to said interior of said reflector, and wherein said mounting means includes means for positioning the probe of the conventional hand-held ophthalmic transilluminator to direct light through said illumination aperture.

18. A glare tester attachment for use with a conventional hand-held ophthalmoscope having a source of illumination, said glare tester attachment comprising:
    a generally concave reflector, said reflector comprising a wall partially enclosing a hollow interior chamber, said wall having an interior light-reflecting surface;
    mounting means for removably supporting said reflector on the conventional hand-held ophthalmoscope;
    means for directing said illumination to said interior light reflecting surface;
    wherein said hollow interior chamber has an open side and a closed side and said reflector has an apex located opposite said open side; and
    wherein said reflector has a viewing aperture generally at said apex of said reflector.

19. The glare tester attachment of claim 18, wherein said mounting means includes a socket for receiving the conventional hand-held ophthalmoscope.

20. The glare tester attachment of claim 18, wherein said means for directing illumination includes a mirror for directing light from the conventional hand-held ophthalmoscope into said interior of said reflector.

* * * * *